(12) United States Patent
Medina

(10) Patent No.: US 11,911,374 B2
(45) Date of Patent: Feb. 27, 2024

(54) METHODS AND USES FOR TREATING CANCER

(71) Applicant: NELUM CORPORATION, Research Triangle Park, NC (US)

(72) Inventor: Manuel Hidalgo Medina, Boston, MA (US)

(73) Assignee: NELUM CORPORATION, Durham, NC (US)

( * ) Notice: Subject to any disclaimer, the term of this patent is extended or adjusted under 35 U.S.C. 154(b) by 0 days.

(21) Appl. No.: 17/153,345

(22) Filed: Jan. 20, 2021

(65) Prior Publication Data

US 2022/0071982 A1    Mar. 10, 2022

Related U.S. Application Data

(63) Continuation of application No. PCT/US2020/070080, filed on May 28, 2020.

(Continued)

(51) Int. Cl.

| | |
|---|---|
| *A61K 31/4545* | (2006.01) |
| *A61K 31/337* | (2006.01) |
| *A61K 31/4355* | (2006.01) |
| *A61K 31/454* | (2006.01) |
| *A61K 31/501* | (2006.01) |
| *A61K 31/502* | (2006.01) |
| *A61K 31/517* | (2006.01) |
| *A61K 31/5377* | (2006.01) |

(Continued)

(52) U.S. Cl.
CPC ........ *A61K 31/4545* (2013.01); *A61K 31/337* (2013.01); *A61K 31/4355* (2013.01); *A61K 31/454* (2013.01); *A61K 31/501* (2013.01); *A61K 31/502* (2013.01); *A61K 31/517* (2013.01); *A61K 31/5377* (2013.01); *A61K 31/7068* (2013.01); *A61K 39/3955* (2013.01); *A61P 35/00* (2018.01)

(58) Field of Classification Search
CPC .............. A61K 31/4545; A61K 31/337; A61K 31/4355; A61K 31/454; A61K 31/501; A61K 31/502; A61K 31/517; A61K 31/5377; A61K 31/7068; A61K 39/3955; A61P 35/00
USPC ...................................................... 424/142.1
See application file for complete search history.

(56) References Cited

U.S. PATENT DOCUMENTS

| | | | |
|---|---|---|---|
| 9,814,703 B2 | 11/2017 | Beachy et al. | |
| 2014/0072630 A1 | 3/2014 | Tao | |

(Continued)

FOREIGN PATENT DOCUMENTS

| | | |
|---|---|---|
| RU | 2577278 C2 | 3/2016 |
| WO | WO 2017/100533 | 6/2017 |

OTHER PUBLICATIONS

Royal et al. (J Immunother 2010; 33: 828-833).*

(Continued)

*Primary Examiner* — Yan Xiao
(74) *Attorney, Agent, or Firm* — Casimir Jones, SC; Jeffrey W. Childers

(57) ABSTRACT

The present disclosure includes a method for treating or ameliorating a cancer or the effects of a cancer in a subject in need thereof comprising administering to the subject an effective amount of a hedgehog inhibitor (HHI) or a pharmaceutically acceptable salt thereof, and a chemotherapeutic agent (CTA).

26 Claims, 8 Drawing Sheets

Panc 163

Related U.S. Application Data

(60) Provisional application No. 62/853,842, filed on May 29, 2019.

(51) Int. Cl.
*A61K 31/7068* (2006.01)
*A61K 39/395* (2006.01)
*A61P 35/00* (2006.01)

(56) References Cited

U.S. PATENT DOCUMENTS

2016/0045598 A1* 2/2016 Sabbatino ........ A61K 39/39558
424/156.1
2017/0326118 A1   11/2017 Tas
2018/0030410 A1*  2/2018 Loh .................. C12N 5/0657

OTHER PUBLICATIONS

Chaudhuri, T.R., et al., "Tumor-priming smoothened inhibitor enhances deposition and efficacy of cytotoxic nanoparticles in a pancreatic cancer model", Mol. Can. Ther., (Jan. 2016), vol. 15, No. 1, pp. 84-93.

Katoh, M., "Genomic testing, tumor microenvironment and targeted therapy of hedgehod-related human cancers", Clinical Science (2019), vol. 133, pp. 953-970.

Xie, H., et al., "Recent advances in the clinical targeting hedgehog/GLI signaling in cancer", Cells (2019), vol. 8, No. 394, pp. 1-17.

International Search Report for PCT/US2020/070080, dated Sep. 11, 2020.

Di Magno et al., Digging a hole under Hedgehog: downstream inhibition as an emerging anticancer strategy. Biochim Biophys Acta. Aug. 2015;1856(1):62-72.

Kim et al., Itraconazole and arsenic trioxide inhibit Hedgehog pathway activation and tumor growth associated with acquired resistance to smoothened antagonists. Cancer Cell. Jan. 14, 2013;23(1):23-34.

Peer et al., Next-Generation Hedgehog/GLI Pathway Inhibitors for Cancer Therapy. Cancers (Basel). Apr. 15, 2019;11(4):538.

Extended EP Search Report for EP 20814240.6, dated Mar. 24, 2023, 16 pages.

Ibuk et al., TAK-441, a novel investigational smoothened antagonist, delays castration-resistant progression in prostate cancer by disrupting paracrine hedgehog signaling, International Journal of Cancer 2013, vol. 133, issue 8, pp. 1955-1966.

Pokataev et al., Systematic drug therapy of metastatic pancreatic cancer, Journal of Modern Oncology, 2016, vol. 18, No. 1, pp. 20-24.

Search Report for RU 2021138875, dated Oct. 12, 2023, 2 pages.

* cited by examiner

METHODS AND USES FOR TREATING CANCER

CROSS REFERENCE TO RELATED APPLICATION

This application claims the benefit of International Application No. PCT/US2020/070080, filed May 28, 2020, which claims the benefit of U.S. Provisional Patent Application No. 62/853,842, filed May 29, 2019, the entire contents of each of which are hereby incorporated herein by reference.

FIELD OF THE INVENTION

The present disclosure includes a method or use for treating or ameliorating a cancer or the effects of a cancer in a subject in need thereof comprising administering to the subject an effective amount of a hedgehog inhibitor (HHI) or a pharmaceutically acceptable salt thereof, and a chemotherapeutic agent (CTA).

BACKGROUND

One feature characteristic of pancreatic cancer is its stroma, which is typically very dense and fibrous. Focusing on the stroma is emerging as a new strategy in the treatment of pancreatic cancer, and different approaches are currently being tested. For example, preclinical and clinical studies with Nab-P indicate that one of the mechanisms by which the drug exerts its effects is by eliminating the tumor stroma of pancreatic cancer. The elimination is accompanied by an improvement in tumor vascularization and a greater penetration of the drug into the cancer cells, which may enhance the antitumor efficacy. Subsequent clinical studies in patients treated with Nab-P have observed similar findings, while also demonstrating that tumors treated with the combination of Gem and Nab-P become more elastic when measuring their elasticity by elastography. Other agents directed against the stroma of pancreatic cancer are being developed, including PEGPH20, a pegylated hyaluronidase that is showing interesting results in patients with tumors high in hyaluronic acid.

One therapeutic target studied in pancreatic cancer is the Hedgehog (Hh) pathway. In preclinical studies, the inhibition of Smo by a cyclopamine analog (IPI-926) resulted in selective stromal elimination, better tumor vascularization, and greater effect of Gem chemotherapy in these models. Based on these studies, a series of clinical trials with Smo inhibitors in combination with Gem was initiated with a hypothesis that stromal elimination and better vascularization may be associated with better drug distribution and greater activity. Despite the promising preclinical data, however these studies did not show better results.

Subsequent preclinical studies in which Smo is genetically removed (by gene deletion), or of chronic treatment with Smo inhibitors, show results that may explain negative data from clinical trials. In these studies, the chronic elimination of the stroma results in a marked increase in the vascularization of the tumor and in the proliferation of the malignant cells which, in a sustained manner, result in a greater number of metastases and lower survival in the treated animals.

The Hedgehog (Hh) pathway is a major regulator of many fundamental processes in vertebrate embryonic development including stem cell maintenance, cell differentiation, tissue polarity and cell proliferation. The Hh signaling pathway exerts its biological effects through a signaling cascade that culminates in a change of balance between activator and repressor forms of glioma-associated oncogene (Gli) transcription factors. The components of the Hh signaling pathway involved in the signaling transfer to the Gli transcription factors include Hedgehog ligands (Sonic Hh [SHh], Indian Hh [IHh], and Desert Hh [DHh]), Patched receptor (Ptch1, Ptch2), Smoothened receptor (Smo), Suppressor of fused homolog (Sufu), kinesin protein Kif7, protein kinase A (PKA), and cyclic adenosine monophosphate (cAMP). The activator form of Gli travels to the nucleus and stimulates the transcription of the target genes by binding to their promoters. The main target genes of the Hh signaling pathway are PTCH1, PTCH2, and GLI1.

Constitutive activation of the Hh pathway leading to tumorigenesis is seen in basal cell carcinomas and medulloblastoma. A variety of other human cancers also demonstrate inappropriate activation of this pathway. Deregulation of the Hh signaling pathway is associated with developmental anomalies and cancer, including Gorlin syndrome, and sporadic cancers, such as pancreatic, breast, colon, ovarian, and small-cell lung carcinomas. The aberrant activation of the Hh signaling pathway is caused by mutations in the related genes (ligand-independent signaling) or by the excessive expression of the Hh signaling molecules (ligand-dependent signaling—autocrine or paracrine). Paracrine Hh signaling from the tumor to the surrounding stroma was recently shown to promote tumorigenesis. This pathway has also been shown to regulate proliferation of cancer stem cells and to increase tumor invasiveness. Targeted inhibition of Hh signaling may be effective in the treatment and prevention of many types of human cancers.

Several Hh signaling pathway inhibitors, such as vismodegib and sonidegib, have been developed for cancer treatment. These drugs are regarded as promising cancer therapies, especially for patients with refractory/advanced cancers. Other Hedgehog inhibitors include TAK 441, taladegib, sonidegib, saridegib (patidegib) BMS833923 and LEQ506

As described by Ohashi et al., the pyrrolo[3,2-c]pyridine derivative, TAK-441, suppressed transcription factor Gli1 mRNA expression in tumor-associated stromal tissue and inhibited tumor growth (treatment/control ratio, 3%) in a mouse medulloblastoma allograft model owing to the improved PK profile based on increased solubility. See, Ohashi et al., *Discovery of the investigational drug TAK-441, a pyrrolo[3,2-c]pyridine derivative, as a highly potent and orally active hedgehog signaling inhibitor Modification of the core skeleton for improved solubility*, Bioorganic & Medicinal Chemistry, Vol. 20, Issue 18, 15 Sep. 2012, herein incorporated by reference with regard to such background teaching.

TAK-441 is 6-ethyl-N-[1-(hydroxyacetyl)piperidin-4-yl]-1-methyl-4-oxo-5-(2-oxo-2-phenylethyl)-3-(2,2,2-trifluorethoxy)-4,5-dihydro-1H-pyrrolo[3,2-c]pyrdine-2-carboxamide, Formula (I):

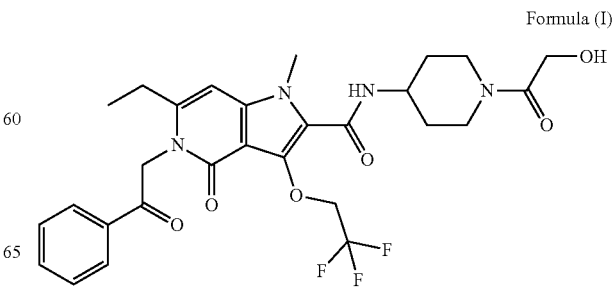

Formula (I)

Methods for synthesizing TAK-441 are disclosed in U.S. Pat. Nos. 8,217,176 and 8,399,449, each of which is incorporated herein by reference in their entirety. Additionally, International Application No. PCT/JP2017/003453, WO 2017/135259, discloses certain co-crystal forms of TAK-441 with L-malic or L-tartaric acid, which is also incorporated herein by reference in its entirety. Such co-crystal forms may be used in the methods of the present disclosure.

There is a need for improved cancer treatments utilizing hedgehog inhibitors.

SUMMARY OF THE INVENTION

One embodiment of the present disclosure includes a method for treating a subject having a cancerous tumor, the method comprising transient administration of a hedgehog inhibitor (HHI) to the subject in combination with one or more additional cancer therapies. One embodiment of the present disclosure includes a method of transiently administering a hedgehog inhibitor (HHI) to a cancer patient in combination with one or more additional cancer therapies, wherein the administration of the HHI is discontinued prior to initiating clinically significant detrimental fibroblast depletion.

In one aspect, the HHI is administered prior to the administration of at least one additional cancer therapies. In one aspect, the administration of the HHI is discontinued prior to discontinuation of at least one of the additional cancer therapies. In one aspect, at least one of the additional cancer therapies is a systemically delivered therapy. In one aspect, the systemically delivered therapy is chemotherapy, targeted therapy, or immunotherapy. In one aspect, the additional cancer therapy is administration of a chemotherapeutic agent (CTA) and the HHI is administered prior to administering the CTA. In one aspect, administration of the HHI is discontinued prior to discontinuation the CTA. In one aspect, the tumor is a fibrotic tumor. In one aspect, the tumor is a solid tumor. In one aspect, the tumor has high stromal content. In one aspect, the HHI reduces stromal content. In one aspect, the HHI induces angiogenesis in or around the tumor. In one aspect, the HHI improves tumor uptake of a subsequently administered CTA. In one aspect, the administration of the HHI is discontinued such that the further reduction of the stroma is halted or clinically insignificant. In one aspect, the administration of the HHI is discontinued such that the further depletion of tumoral fibroblasts is halted or clinically insignificant. In one aspect, the administration of the HHI improves the effect of the additional cancer therapy but is discontinued prior to promoting clinically significant tumor growth. In one aspect, the administration of the HHI is discontinued such that administration of the HHI does not subsequently initiate clinically significant, HHI-induced metastasis. In one aspect, the administration of the HHI is discontinued such that administration of the HHI does not significantly increase the likelihood of subsequent tumor metastasis. In one aspect, the administration of the HHI improves the efficacy of the subsequently administered cancer therapy. In one aspect, the improvement is evidenced by one or more of: metabolic responses, positron emission tomography, objective responses according to criteria, progression-free survival, overall survival, responses based on levels of a tumor marker, toxicity, and elasticity of the tumor. In one aspect, the improvement is evidenced by extended survival or extended time to disease progression. In one aspect, the improvement is evidenced by progression free survival. In one aspect, the cancer is pancreatic cancer, esophageal cancer, squamous cell carcinoma, prostate cancer, colon cancer, breast cancer, hepatocellular carcinoma, renal cancer, or cholangiocamcinoma. In one aspect, the cancer is pancreatic ductile adenocarcinoma (PDAC). In one aspect, the cancer is hepatocellular cancer. In one aspect, the HHI is an Smo antagonist. In one aspect, the Smo antagonist is selected from the group consisting of TAK 441, glasdegib, taladegib, sonidegib, saridegib, patidegib, BMS833923, LEQ506, and a combination thereof. In one aspect, the HHI is TAK 441. In one aspect, the CTA is selected from the group consisting of gemcitabine, nab-paclitaxel, taxol, irinotecan, temozolomide, capecitabine, topotecan, cisplatin, oxaliplatin, carboplatin, camptothecin, cytarabine, fluorouracil, cyclophosphamide, etoposide phosphate, teniposide, doxorubicin, daunorubicin, and pemetrexed. In one aspect, the CTA is one or more of nab-paclitaxel, gemcitabine, and cisplatin. In one aspect, the CTA is one or more of nab-paclitaxel and gemcitabine. In one aspect, the route of administration for the HHI is selected from the group consisting of intravenous, oral, and topical. In one aspect, the route of administration for the additional cancer therapy is selected from the group consisting of intravenous, oral, and topical. In one aspect, the doses of the HHI and additional cancer therapy are administered between the biologically effective dose and the maximum tolerated dose. In one aspect, the patient receives cycles of treatment and the additional cancer therapy is a CTA is administered during all or substantially all of the cycles of treatment. In one aspect, the patient receives cycles of treatment of the additional cancer therapy and the HHI is administered during fewer than all of cycles of treatment. In one aspect, the patient is receiving treatment of the additional cancer therapy in cycles and the one or more doses of HHI is only administered prior to and during the early treatment cycles. In one aspect, the one or more doses of HHI is only administered 1-10 days prior to chemotherapy for 1-5 cycles. In one aspect, the one or more doses of HHI is administered no later than the third cycle. In one aspect, each cycle is 28 days and the HHI is administered on days −4 to −1 and 10-13 of each cycle of cycles 1-3 and the CTA is administered on days 1, 8, and 15, every 28 days. In one aspect, the HHI is 800 mg dose of TAK 441. In one aspect, the CTA is selected from one or more of 1000 mg/m$^2$ of Gemcitabine and 125 mg/m$^2$ nab-paclitaxel. In one aspect, the one or more doses of an additional cancer therapy are followed by one or more doses of a Checkpoint Inhibitor (CI). In one aspect, the CTA is a Checkpoint Inhibitor (CI) administered in one or more doses. In one aspect, the route of administration for the CI is selected from the group consisting of intravenous, oral, or topical. In one aspect, the one or more doses of the CI are administered between the biologically effective dose and the maximum tolerated dose. In one aspect, the CI is a CTLA 4 inhibitor, a PD1 inhibitor, or a PDL1 inhibitor. In one aspect, the CI is Tremelimumab, Ipilimumab, Durvalumab, Nivolumab, Pembrolizumab, Atezolizumab, Cemiplimab, AGEN1884, AGEN2034, or AGEN1181. In one aspect, the CI is Ipilimumab. In one aspect, the patient receives treatment in cycles and the one or more doses of CI is only administered near the end of or the beginning of a treatment cycle. In one aspect, the one or more doses of CI is only administered within 7 days of the end of a treatment cycles. In one aspect, the one or more doses of CI is only administered after at least one, two or three treatment cycles. In one aspect, the cycle is 28 days and the CI is administered on days 1 and 21 of each cycle, starting with cycle 4. In one aspect, the CI dose is a 3 mg/kg IV dose of Ipilimumab.

One embodiment of the present disclosure includes method for treating or ameliorating a cancer or the effects of a cancer in a subject in need thereof comprising administering to the subject an effective amount of a hedgehog inhibitor (HHI) or a pharmaceutically acceptable salt thereof, and a chemotherapeutic agent (CTA).

In one aspect, the HHI is TAK 441. In one aspect, the CTA is nab-paclitaxel. In one aspect, the CTA is a Checkpoint Inhibitor (CI). In one aspect, the method further comprises administration of a Checkpoint Inhibitor (CI). In one aspect, the cancer has fibrotic stroma. In one aspect, the cancer is pancreatic cancer, esophageal cancer, squamous cell carcinoma, prostate cancer, colon cancer, breast cancer, hepatocellular carcinoma, renal cancer, or cholangiocarncinoma. In one aspect, the cancer is pancreatic adenocarcinoma (PDAC). In one aspect, the cancer is hepatocellular carcinoma. In one aspect, treatment effect is measured by tumor regression. In one aspect, treatment effect is measured by a tumor growth inhibition factor in a tumor growth inhibition model selected from one or more of the group consisting of: metabolic responses, as measured by fluorodeoxyglucose (FDG), PET according to EORTC criteria), objective responses according to RECIST (Response Evaluation Criteria in Solid Tumors) criteria, Progression Free Survival, Overall Survival, responses based on levels of a tumor marker (e.g. CA 19.9), toxicity (e.g. according to Common Toxicity Criteria for Adverse Events Terminology, National Cancer Institute, version 4.03 (NCI CTCAE v4.03)), and Elasticity of the tumor.

One embodiment of the present disclosure includes the methods herein described as use of the recited agent(s) for the treatment of the recited diseases or disorders.

One embodiment of the present disclosure includes the methods herein described as use of the recited agent(s) in the manufacture of a medicament for the treatment of the recited diseases or disorders.

One embodiment of the present disclosure includes the use of the recited agent(s) for the treatment of the recited diseases or disorders.

One embodiment of the present disclosure includes the use of the recited agent(s) as medicaments for the treatment of the recited diseases or disorders.

One embodiment of the present disclosure includes a pharmaceutical composition comprising the recited agent(s) for the treatment of the recited diseases or disorders.

One embodiment of the present disclosure includes the recited agent(s) suitable for use in the treatment of the recited diseases or disorders.

One or more aspects and embodiments may be incorporated in a different embodiment although not specifically described. That is, all aspects and embodiments may be combined in any way or combination.

DETAILED DESCRIPTION OF THE INVENTION

Definitions

Figure 1:
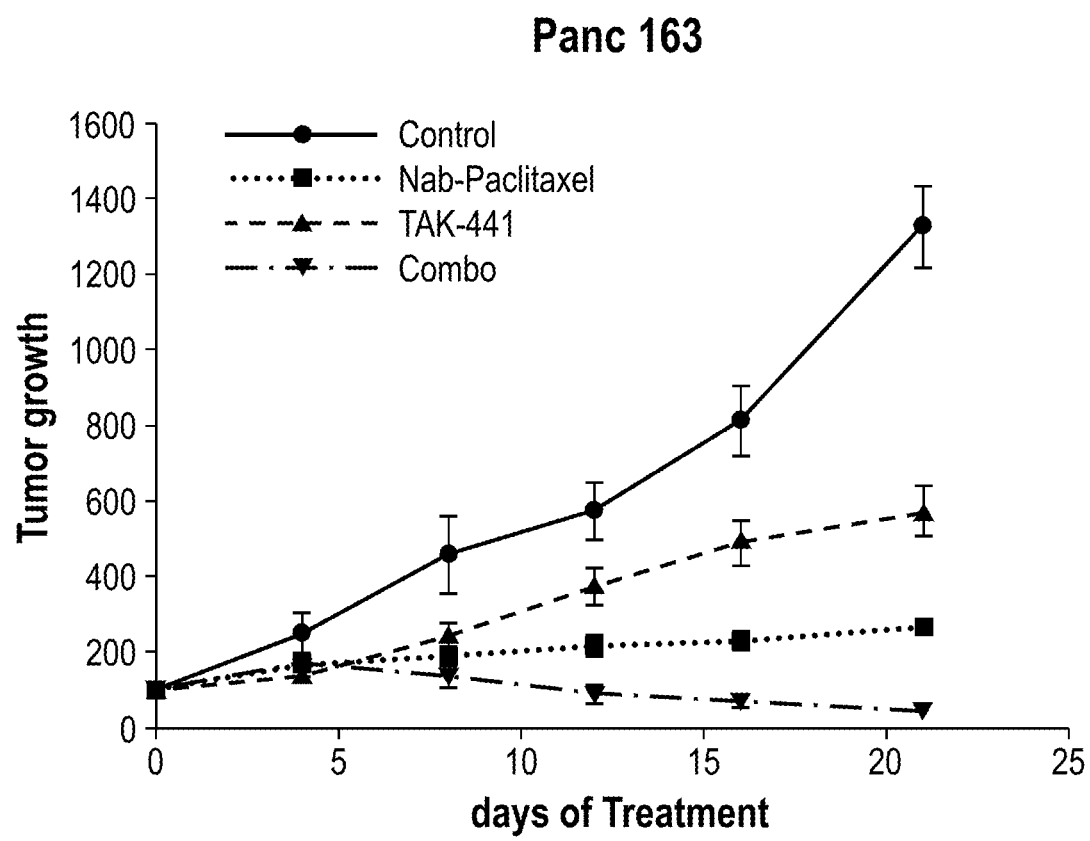
FIG. 1 shows tumor growth (% referred to the tumor initial volume) of Panc163 model treated with the indicated regimens. Tumors were implanted subcutaneously.

As used herein, "treatment" (also "treat" or "treating") refers to any medical intervention or administration of a substance that partially or completely alleviates, ameliorates, relives, inhibits, delays onset of, reduces severity of, or reduces incidence of one or more symptoms, features, or causes of a particular disease, disorder, or condition.

As used herein, "transient administration of an agent" refers to administration that is discontinued, either permanently or for a set period of time, such that administration does not continue throughout all cycles of the treatment.

As used herein, "cancer," "malignancy," "neoplasm," "tumor," and "carcinoma" may be used interchangeably and refer to cells that exhibit abnormal, uncontrolled, or autonomous growth.

As used herein, "chemotherapeutic agent" refers to one or more of a pro-apoptotic, cytostatic, or cytotoxic agent.

As used herein, "clinically significant" refers, without limitation, to that which merits consideration for, or has an impact on, clinical decision-making.

As used herein, the term "clinical" refers to information pertaining to or founded on actual observation and treatment of patients, as distinguished from theoretical or basic sciences.

As used herein, the phrase "dosing regime" or, alternatively, "therapeutic regimen" refers to a set of unit doses, typically more than one, that may be administered individually to a subject, typically separated by a period of time.

As used herein, "time to disease progression" ("TTP") refers to the time, generally measured in weeks or months, from the time of initial treatment until the cancer progresses or worsens. Such progression can be determined through testing or observation, such as being evaluated by a skilled clinician.

As used herein, "extending TTP" refers to increasing the time until disease progression in a treated patient relative to an untreated patient.

As used herein, "survival" refers to a patient remaining alive, and includes overall survival as well as progression-free survival.

As used herein, "overall survival" refers to a patient remaining alive for a defined period of time, such as 1 year, 5 years, or longer, from the time of either diagnosis or treatment.

As used herein, "progression-free survival" refers to a patient remaining alive, without the cancer progressing or getting worse. Such progression can be determined through testing or observation, such as being evaluated by a skilled clinician.

As used herein, "extending survival" refers to increasing overall or progression free survival in a treated patient relative to an untreated patient.

As used herein, relative terms of therapeutic achievement, such as "improve," "increase," or "reduce" or grammatical equivalents thereof, indicate values or conditions that are relative to a baseline measurement or condition, such as a measurement in the same individual prior to initiation of a treatment described herein, or a measurement in a control individual (or multiple control individuals) in the absence of the treatment described herein.

As used herein, "biologically effective dose" refers to the amount of an absorbed compound that reaches targets or sites of action within the body to cause a biologic effect.

As used herein "maximum tolerated dose" (or MTD) refers to the highest dose of a drug or treatment that does not cause unacceptable side effects.

As used herein, "cycle" refers to a treatment regimen given over a period of time.

As used herein, "fibrotic response to malignancies" refers to an increase or decrease in fibroid development and or persistence in a tumor.

As used herein, "tumor regression" refers to a halting of growth or a decrease in size, mass, or number of tumor bodies or tissue.

As referenced hereinabove, TAK-441 is an investigational small molecule that is administered orally and inhibits Smo. In an in vitro model, TAK-441 inhibited the binding of cyclopamine, a human Smo inhibitor, to a 50% inhibitory concentration ($IC_{50}$) of 8.6 nM. In murine models of castration-resistant prostate cancer, TAK-441 was shown to inhibit the paracrine signaling of the Hh ligand, and thus inhibit tumor progression.

TAK-441 was studied in a phase I trial with participating Spanish sites. This recently published trial studied the safety, tolerance, pharmacokinetics, and preliminary clinical activity of a single dose and multiple doses of TAK-441. A total of 34 patients were included (median age: 59 years, range: 28-82 years) with solid tumors in advanced stages (colorectal cancer (26%), basal cell carcinoma (21%), and pancreatic cancer (9%)). Patients received a daily dose of oral TAK-441 (PO) that ranged between 50-1600 mg. That daily dose was doubled in each cohort subsequently until the maximum tolerated dose (MTD) was reached. Blood samples were collected to evaluate plasma concentrations of TAK-441 post-dose, as well as skin biopsies to determine the inhibition of Gli1 gene expression.

The MTD was established at 1600 mg/day, based on the size of the tablet and its potency. The dose-limiting toxicities included muscle spasms and fatigue. Oral absorption was quite rapid, with the mean maximum time ($T_{max}$) being 1.8-4.2 hours after the administration of a single dose, and 2.4-4.0 hours after administration of several doses. The median elimination half-life was 12.9-18.3 hours. The pharmacokinetics of TAK-441 based on the area under the curve (AUC) of plasma concentration-time was linear over the entire dose range. Inhibition of Gli1 gene expression in skin biopsies was observed with all doses analyzed.

As noted, the present disclosure includes a method for treating a subject having a cancerous tumor. The method includes transient administration of a hedgehog inhibitor (HHI) to the subject in combination with one or more additional cancer therapies. The additional cancer therapies may be selected from the group consisting of, but not limited to, chemotherapy, immunotherapy, and targeted therapy. The present disclosure further includes a method of transiently administering an HHI to a cancer patient in combination with one or more additional cancer therapies is provided, wherein the administration of the HHI is discontinued prior to initiating clinically significant detrimental fibroblast depletion, including but not limited to systemic side effects such as developing cachexia, anemia, and other paraneoplastic syndromes as well as induction of immunosuppression and acceleration of cancer.

In this regard, reduction of stroma and induction of vascularization may be considered positive as they allow for better delivery of a chemotherapy agent. Fibrotic tumors have low vessel density and are hypo vascular. For these reasons, drugs cannot penetrate fibrotic tumors. Thus, induction of vascularization would improve uptake of drug. There is a fine balance, however, between this effect being positive, and then turning detrimental. When fibrosis is eliminated, or overly restricted, the tumor becomes too vascularized, and that leads to higher metastasis and shorter patient survival.

TAK-441 is being developed for oral use in the treatment of advanced hematological and non-hematological malignancies. Preclinical studies have determined that TAK-441 is orally bioavailable in multiple species. TAK-441 inhibited Gli transcriptional activity at a concentration that produced a 50% inhibition ($IC_{50}$) of 4.4 nM in the luciferase-Gli-sensitive (Gli-luc) promoter assay in cells/Gli-luc NIH3T3. TAK-441 also inhibits the expression of Gli1 mRNA with a concentration that produced an $IC_{50}$ of 1.9 nM in MRC5 human embryonic fibroblasts. In addition, TAK-441 inhibits the binding of cyclopamine to human Smo (hSmo) in 293T cells overexpressing hSmo with an $IC_{50}$ of 8.6 nM. These data suggest that TAK-441 inhibits the Hh signaling pathway through its binding to Smo.

The administration of TAK-441 in an allograft model of medulloblastoma with mutations in Ptch1 (+/−) (Ptch1 heterozygote) and p53 (−/−) (p53 null) or the mouse xenograft model PAN-04 primary human pancreas resulted in dose-dependent inhibition of mouse or stromal tumor associated with the expression of Gli1 mRNA in vivo, respectively. TAK-441 demonstrated a significant dose-dependent tumor activity in these models (p<0.025). In addition, the combination of TAK-441 and rapamycin, an inhibitor of mTOR (mammalian target of rapamycin) showed a better antitumor activity in combination compared to the activity of any agent alone in the PAN-04 mouse model of pancreatic cancer.

Pharmacokinetics in Vivo

TAK-441 is characterized by a low CL (161.3 and 397.9 ml/h/kg), a moderate distribution volume in steady state plasma (Vss) (681.6 and 2181.3 ml/kg), and a moderate t ½ (1.7 and 9.8 hours), with an oral bioavailability in rats and dogs of 31.7% and 90.3%, respectively. There were no differences in plasma exposure between sexes, either in rats or dogs. Regarding the effect of food, in dogs, an increase of approximately 2 times the degree of absorption was observed when TAK-441 was dosed to fed dogs (in comparison with fasting dogs), producing an increase in both $C_{max}$ and the area under the plasma concentration against the time curve from 0 to 24 hours (AUCO-24 h).

At a concentration of 1.73 mM, TAK-441 has a high binding to plasma proteins in mice (99.7%) and rats (96.2%) and a lower binding in both dogs (79.6%) and in human beings (87.7%). TAK-441 is metabolized to metabolites not identified through cytochrome P450 (CYP) isoenzyme CYP3A4/5 after oral administration to rats and dogs. No metabolite characteristic of humans was detected when incubations of hepatic microsomes were performed. TAK-441 is a weak inhibitor of CYP2C8 and had no inhibitory effect on other CYP isozymes. TAK-441 is not a time-dependent inhibitor of the CYP isoenzyme in human liver microsomes. Therefore, there is a low potential for TAK-441 to affect the pharmacokinetics of other CYP3A4/5 substrates administered concomitantly. However, concomitant administration of CYP3A inhibitors and/or inducers may affect the pharmacokinetics of TAK-441. TAK-441 has a high permeability (Papp, A-to-B 19.6 '10-6 cm/sec; Papp, B-to-Un 37.8 '10-6 cm/sec) in Caco-2 cells, being a bad substrate for P-glycoprotein (P-gp) flow pump, as well as a weak inhibitor of P-gp ($IC_{50}$ of 6.59 mM).

Safety Pharmacology

The biochemical activity of TAK-441 (at a concentration of 10 mM) was carried out in a total of 126 tests. Among the enzymes, receptors and transporters included in the TAK-441 assays, it inhibited an enzyme, human PDE4 phosphodiesterase, as well as a transporter, the human neurotransmitter dopamine, by more than 50% (67% and 75%, respectively).

Toxicology Studies

In toxicological studies according to Good Laboratory Practices (GLP), TAK-441 administration was to rats and dogs at exposures exceeding the predicted concentration to achieve efficacy was associated with a variety of changes that can be attributed to pharmacological inhibition of the Hh signaling pathway. These changes include: decreased body weight; atrophy of the growth plate in the ribs and hair follicles; erosion or ulceration of the gastric mucosa; anemia; necrosis and hypocellularity of the bone marrow as well as inflammation and hemorrhage in the lung. The dose-limiting toxicities observed in dogs consisted of weight loss; decrease in food consumption; injuries of the gastrointestinal tract (vomiting, diarrhea, anorexia, weight loss, ulceration and bleeding). Each of these effects is considered susceptible to follow-up both clinically and through laboratory tests.

The results of the studies conducted with TAK-441 indicate that the clinically relevant changes observed, including the alteration in the hematological parameters, gastrointestinal disorders, decreased appetite and weight loss, are reversible. Isolated changes for which reversibility was not demonstrated included atrophy of the growth plate in the hair follicles and bones and alterations in the incisors. Both the atrophy of the growth plate and the alteration of the incisors are not considered relevant toxicological findings in the case of clinical administration of TAK-441 to adult patients with cancer because in adult patients, the growth plates are already closed, and the incisor teeth have already matured. On the other hand, the gait alterations and tremors observed in the rats are of unknown relevance to humans and are susceptible to clinical follow-up.

TAK-441 Phase 1 Trial

As summarized hereinabove, TAK-441 has been evaluated in a phase 1 study in patients with advanced cancer. A total of 34 patients were included (median age: 59 years, range: 28-82 years) with solid tumors in advanced stages (colorectal cancer (26%), basal cell carcinoma (21%), and pancreatic cancer (9%)). Patients received a daily dose of TAK-441 PO that ranged between 50-1600 mg. The daily dose was doubled in each cohort subsequently until the maximum tolerated dose (MTD) was reached. Blood samples were collected to evaluate the plasma concentrations of TAK-441 after the dose, as well as skin biopsies to determine the inhibition of Gli1 gene expression. The MTD was established at 1,600 mg/day (based on the size of the tablet and its potency). The adverse effects observed are detailed in Table 2. Dose-limiting toxicities included muscle spasms and fatigue. Oral absorption was quite rapid; the mean $T_{max}$ was 1.8-4.2 hrs after the administration of a single dose and 2.4-4.0 hrs after the administration of several doses. The median elimination half-life was 12.9-18.3 hrs. The pharmacokinetics of TAK-441 based on plasma concentration-time AUC was linear over the entire dose range. Inhibition of Gli1 gene expression in skin biopsies was observed with all doses analyzed.

A partial response was observed in a patient with basal cell carcinoma, as well as a stability in disease in seven patients with several solid tumors. TAK-441 is well-tolerated, presenting a MTD of 1600 mg/day, with evidence of antitumor activity.

Chemotherapy Agents (CTA)

Two exemplary CTA include cytostatics, in particular, Gemcitabine ("Gem") and Nab-Paclitaxel ("nab-P") (Abraxane®). Gem has a marketing authorization for patients with locally advanced or metastatic adenocarcinoma of the pancreas. Nab-P (Abraxane®) is a nanoparticle formulation of paclitaxel bound to albumin, which may have considerably different properties compared to other paclitaxel formulations. Nab-P is approved for commercialization by the European Medicines Agency (EMA) in combination with Gem for the treatment of patients with advanced pancreatic cancer.

Both cytotoxins are prepared by pharmacy services and administered intravenously, according to the specifications described in their respective technical data sheets. When possible, the treatment should be administered at the hospital during the day to enable patients to remain ambulatory and at home. Nab-P can be administered as a 30-minute IV infusion followed by a 30-minute IV infusion of Gem.

One typical dose and administration schedule is nab-P 125 mg/m² IV followed by Gem 1,000 mg/m²IV administered on days 1, 8 and 15 in cycles of 28 days.

Additional CTA's include, but are not limited to, taxol, irinotecan, temozolomide, capecitabine, topotecan, cisplatin, oxaliplatin, carboplatin, camptothecin, cytarabine, fluorouracil, cyclophosphamide, etoposide phosphate, teniposide, doxorubicin, daunorubicin, and pemetrexed.

EXAMPLES

Example 1 Targeting Pancreatic Cancer Stroma with TAK441

To determine whether combining of TAK441 and nab-paclitaxel results in anti-tumoral synergism and to assess the effects of sequential promotion and inhibition of blood vessel formation effect, three (3) different Pancreatic Ductal Adenocarcinoma (PDAC) tumors from PancXenoBank (Panc163, JH051, and Panc025) were treated with the combination of nab-paclitaxel (ABI) and TAK-441 (a hedgehog inhibitor).

After several dose-finding studies to define the most feasible dose of nab-paclitaxel, a dose of 50 mg/kg 1dq4×3 was used. TAK-441 was selected and administered daily at the recommended dose (25 mg/kg daily p.o.). The study was conducted for 21 days.

Figure 2:
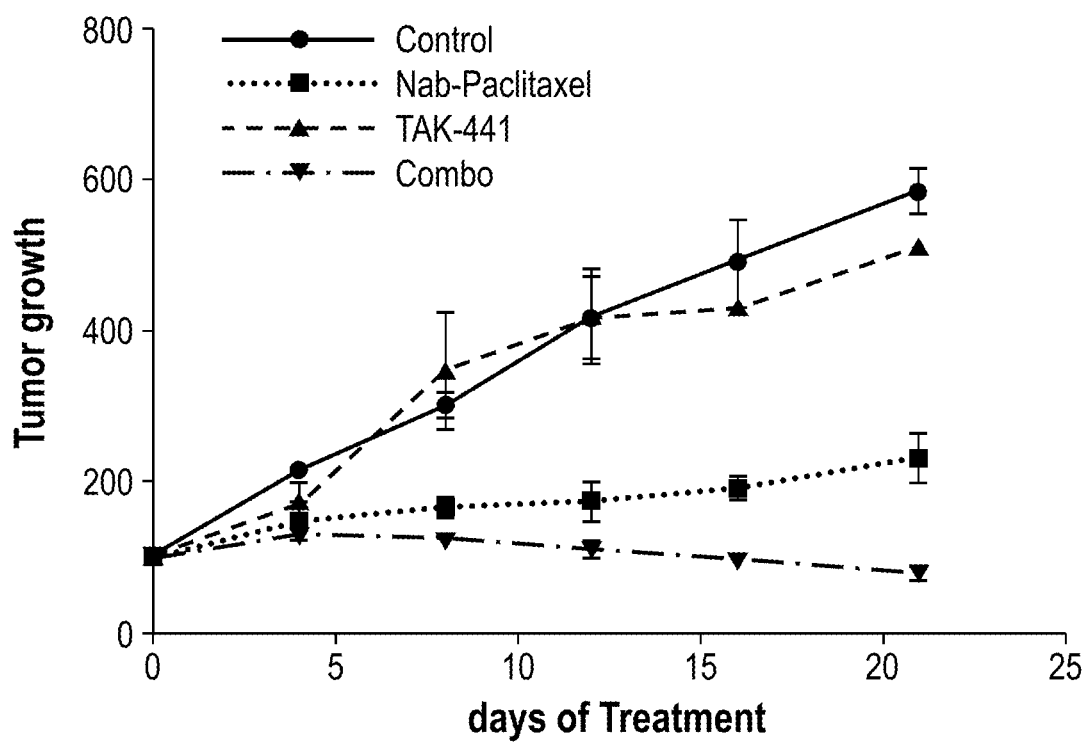
FIG. 2 shows tumor growth (% referred to the tumor initial volume) of JH051 model treated with the indicated regimens. Tumors were implanted subcutaneously FIG. 3. shows tumor growth (% referred to the tumor initial volume) of Panc025 model treated with the indicated regimens. Tumors were implanted subcutaneously.
Figure 3:
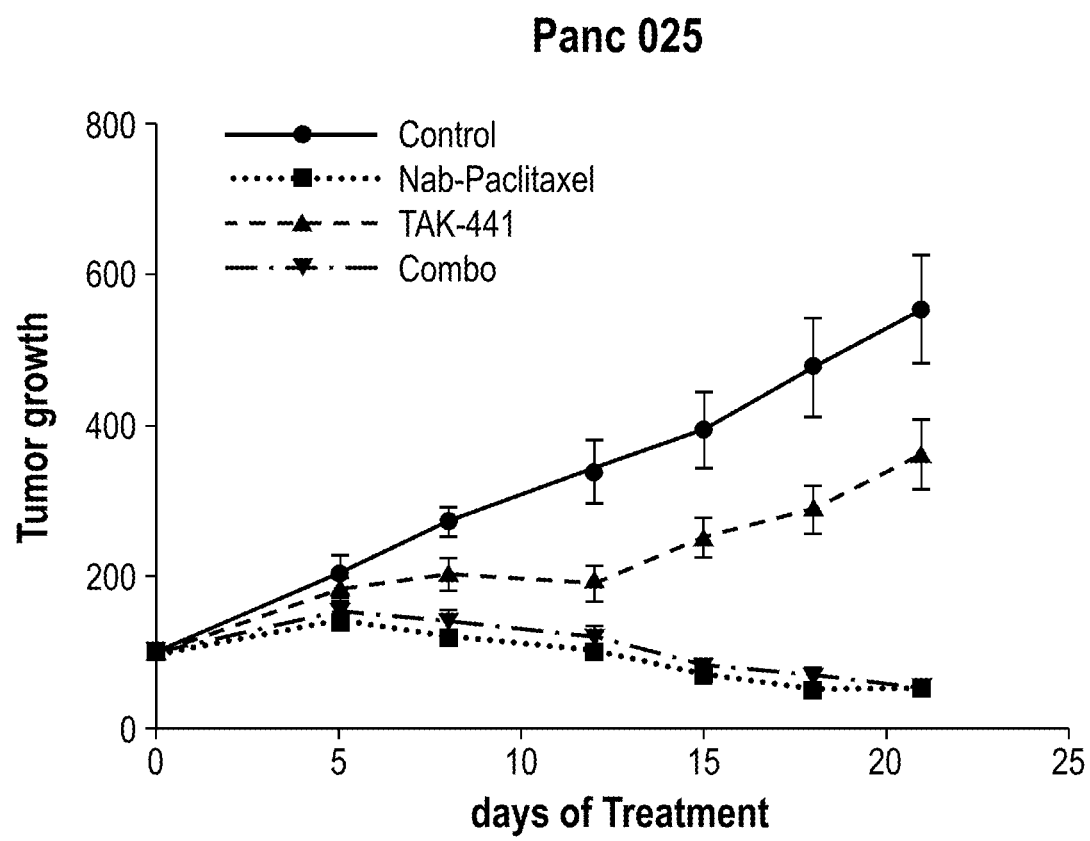

As shown in FIGS. 1-3, the combination of the two agents resulted in synergistic tumor regression in all analyzed models compared to either agent alone.

Based on the tumor volume values on experimental day 21, it was estimated the Tumor Growth Inhibition (TGI) factor as indicated in the Table 1. In all three pancreatic cancer models, the maximum inhibition was observed when mice were treated with the combination of nab-paclitaxel and the anti-stroma agent TAK-441.

TABLE 1

TGI (%) day 21 (1 − [Tf − Ti]/[Cf − Ci])

| MODEL | nab-paclitaxel | TAK-441 | Combo |
|---|---|---|---|
| Panc 163 | 87% | 61% | 105% |
| JH 051 | 73% | 15% | 104% |
| Panc 025 | 110% | 42% | 110% |

In order to evaluate the histological status of the stroma after treatment, Masson's Trichrome stained slides from Panc 163 and Panc 025 models were analyzed.

Figure 4:
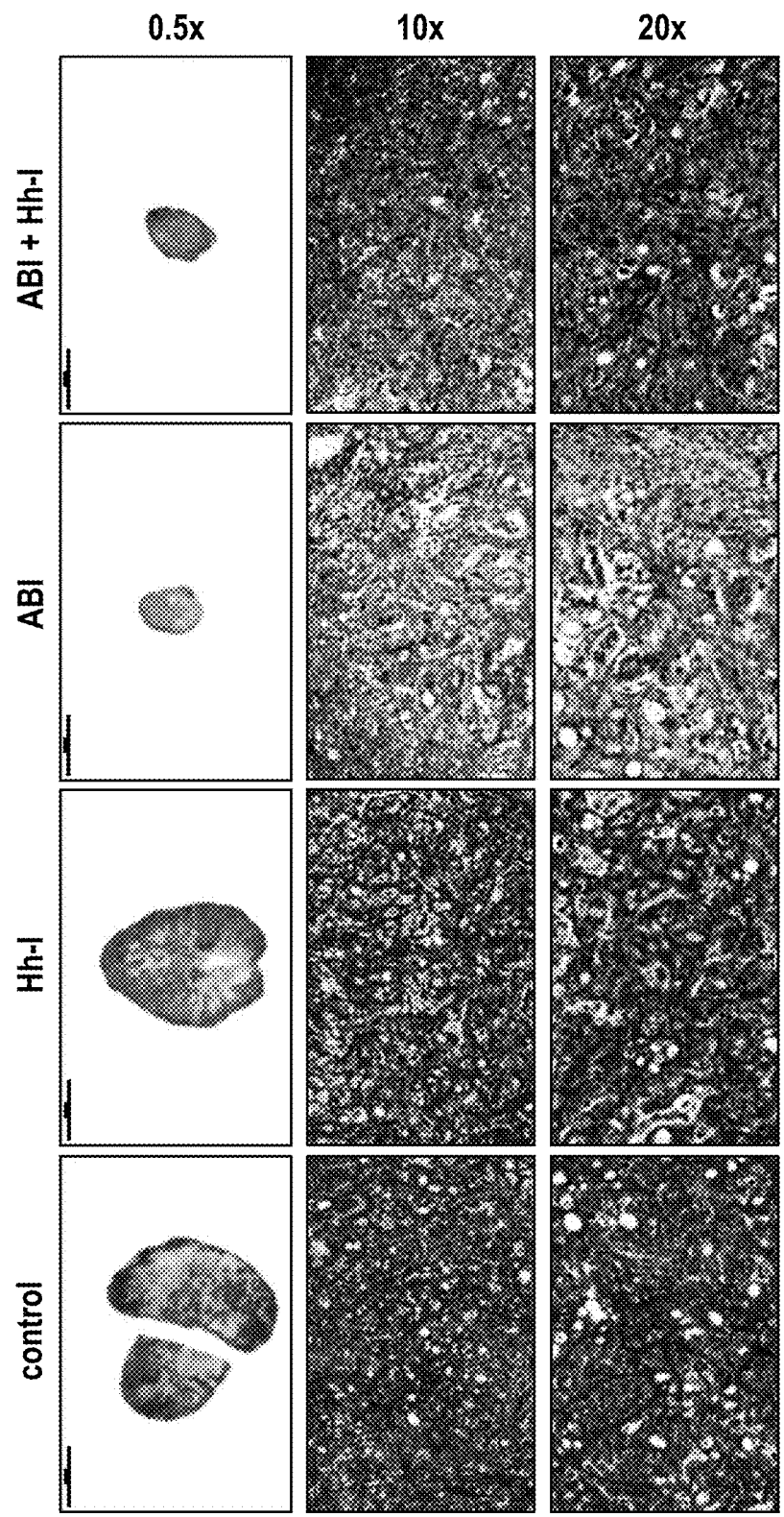
FIG. 4. Representative images of Masson's staining from Panc 163 tumor samples obtained from all the experimental arms.
Figure 5:
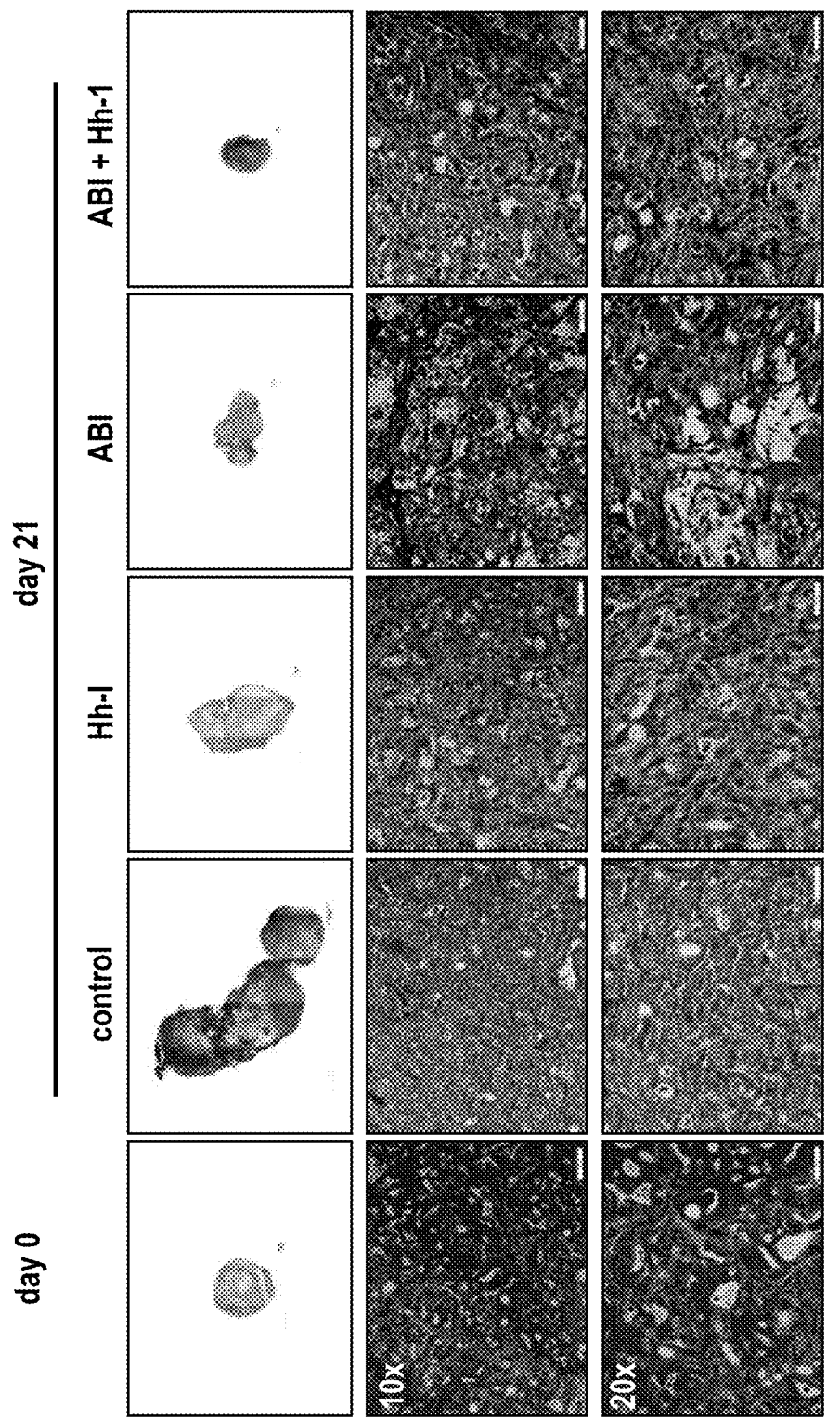
FIG. 5. Representative images of Masson's staining from Panc 025 tumor samples obtained from all the experimental arms. In the first column, it is shown the staining pattern at the treatment starting day.

As it is shown in FIGS. 4 and 5, samples from the ABI treated arms showed more tumor shrinkage and increased presence of fibrosis (as per colagen staining).

Example 2 (Prophetic)

A phase I/II clinical trial that may be one or more of open, multicenter, and non-randomized includes patients, the number of which is selected to be sufficiently powered, for example twenty-five (25), with advanced pancreatic cancer that meet protocol-specified inclusion criteria, are not excluded, or subsequently withdrawn according to relevant criteria and/or protocol.

Patients receive conventional chemotherapy with Gemcitabine (1000 mg/m$^2$ IV) (G) and Abraxane® nab-P (125 mg/m$^2$ IV) (A) on days 1, 8, and 15 of each cycle (every 28 days) according to the conventional treatment scheme. In Cycles 1-3, prior to treatment on days 1 and 15, TAK-441 (also referred to as NLM-001) is administered at a dose of 800 mg/day PO for 4 days followed by a rest day before treatment with chemotherapy. Initially, a subset, such as six (6) patients, are included and observed for toxicity for one treatment cycle. If more than two Grade ≥3 toxic events occur that are related to TAK-441, the dose of the drug is reduced to 400 mg/day.

Tumor elasticity is measured by endoscopic ultrasound with elastography on baseline and on days −1 and 13 of Cycle 1. A biopsy of the primary tumor is carried out simultaneously at baseline and Cycle 1 Day 13. After the first cycle, patients continue treatment until disease progression or unacceptable toxicity.

Figure 6:
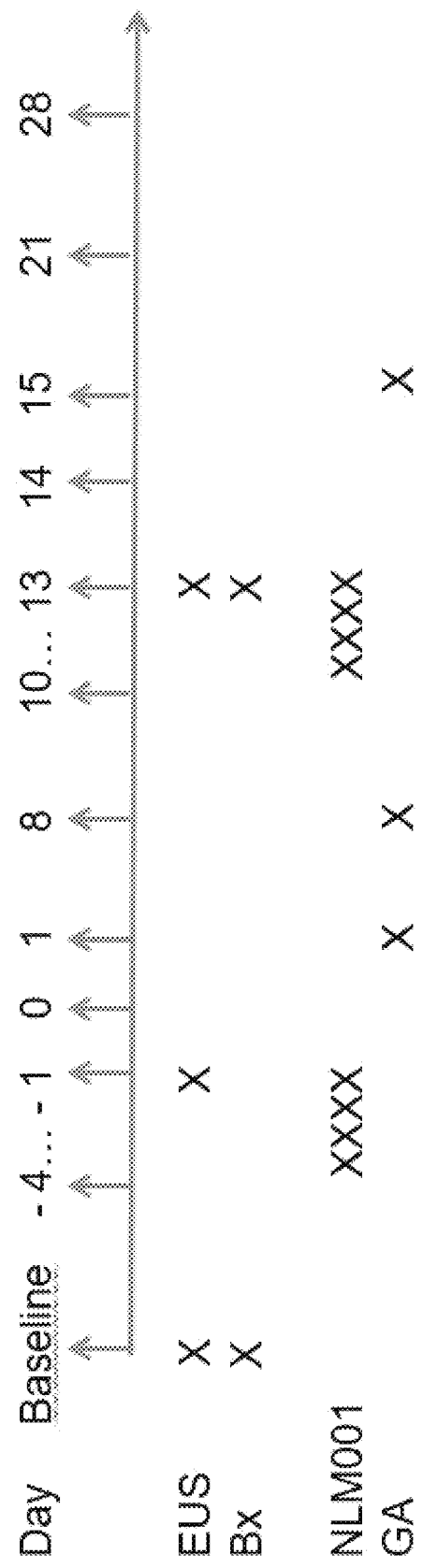
FIG. 6. Treatment scheme in which patients receive conventional chemotherapy with Gemcitabine (1000 mg/m$^2$ IV) (G) and Abraxane® nab-P (125 mg/m$^2$ IV) (A) on days 1, 8, and 15 of each cycle (every 28 days). In Cycles 1-3, prior to treatment on davs 1 and 15, TAK-441 (also referred to as NLM-001) is administered at a dose of 800 mg/dav PO for 4 days followed by a rest day before treatment with chemotherapy. After the first cycle, patients continue treatment until disease progression or unacceptable y. Patients are treated for four (4) cycles, namely four davs on, and four days stop.

Patients are treated for four (4) cycles, namely four days on, and four days stop (see FIG. 6).

Treated patients are believed to show improvement over control patients, including but not limited to improvement in one or more of the following:

Metabolic Responses by FGD PET According to the EORTC Criteria.

Objective response according to the RECIST criteria. Objective response determined by the Response and evaluation criteria in solid tumors (RECIST) v 1.1. These criteria are a set of published standards that define when cancer patients improve, stabilize or worsen during treatments. The results are tabulated according to the different response categories.

Progression Free Survival, Overall Survival: The rate of progression-free survival (PFS) at 3 and 6 months (% PFS-3m; % PFS-6m) defined as the percentage of patients who do not have cancer progression (growth or spread) after 3 or 6 months of enrollment recorded from randomization. Estimates are made by constructing a survival table using the Kaplan-Meier method. For the purposes of statistical analysis, the date corresponding to disease progression is:

i. The scheduled response review when the progression is documented by CT and/or physical examination.

ii. Death from any cause in the absence of previously documented progression.

iii. Start of a second-line treatment after a decision is made to suspend the protocol treatment for any cause, whether for reasons of toxicity or tolerability.

iv. Documentation of progression when the suspension of the protocol treatment has not been followed by a second line treatment.

v. Overall survival is determined from the beginning of treatment to the death of the patient for any cause. It is estimated by constructing a survival table using the Kaplan-Meier method.

Responses Based on Levels of the Tumor Marker CA 19.9

CA 19.9 response is calculated as the maximum percentage of change with respect to baseline in those patients with a baseline higher than 1.25 times the upper limit of normal in the local laboratory of each center. In addition, the results are tabulated according to the categories Responder and Non-responder, for which three different respondent criteria are used: reduction of more than 50%, of more than 75% and of more than 90%, respectively.

Toxicity According to CTCAE NCI v4.03

The safety of the treatment is described by tabulating all of the observed Adverse Effects, including clinical events and laboratory data. They are classified, and their severity quantified in accordance with the Common Terminology Criteria for Adverse Events, National Cancer Institute, version 4.3 (CTCAE-NCI v. 4.3). Disease progression is considered a consequence of the natural history of the disease, so it is be collected in the patient CRF and is not treated as an adverse event in this study. Disease progression therefore is not communicated according to pharmacovigilance procedures, but it must be recorded in the response category, following the measures specified in the protocol.

Tumor Elasticity

A secondary variable of the study is the measurement of the tumor elasticity by elastography defined as the "quotient strain ratio" between the tumor tissue and normal tissue as previously described. A Pentax linear echoendoscope and the Hitachi EUB900 device will be used for its measurement. Areas representative of the tumor and normal surrounding tissue will be selected. The results of the elastography will be expressed through the "quotient strain ratio" between the tumor tissue and the normal tissue. In previous studies, this index has an average value of 32. We hope that with treatment with TAK-441 it will be reduced by at least 50%.

Biomarkers

Expression of Gli-1 mRNA, smooth muscle actin positive cancer associated fibroblast (SMA+CAF), collagen structure and lymphocytic infiltrate (CD3, CD4, and CD8).

Example 3 (Prophetic)

A phase I/II clinical trial that may be one or more of open, multicenter, and non-randomized as in Example 2, additionally adding administration of a checkpoint inhibitor, such as a PD1 or a CTLA4 inhibitor. One example is ipilimumab.

Figure 7:
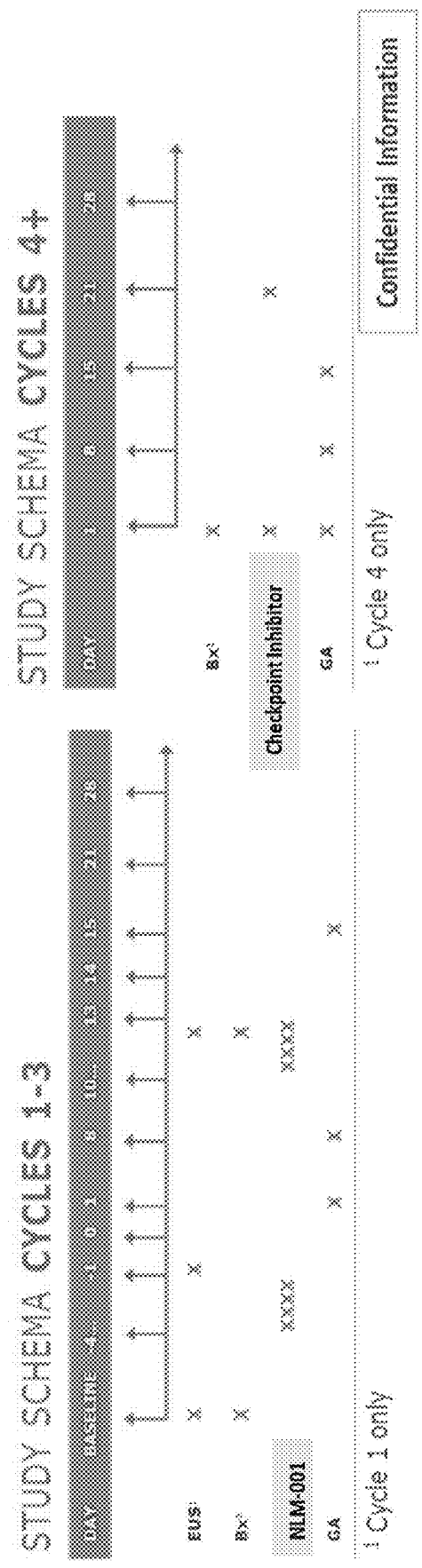
FIG. 7. An example of a treatment scheme in which a 3 mg/kg IV dose of Ipilimumab is administered on days 1 and 21 of each cycle, startinq with cycle 4.

As one example, a 3 mg/kg IV dose of Ipilimumab is administered on days 1 and 21 of each cycle, starting with cycle 4, as illustrated in FIG. 7. Otherwise, the doses and improvement endpoints remain as described in Example 2.

Figure 8:
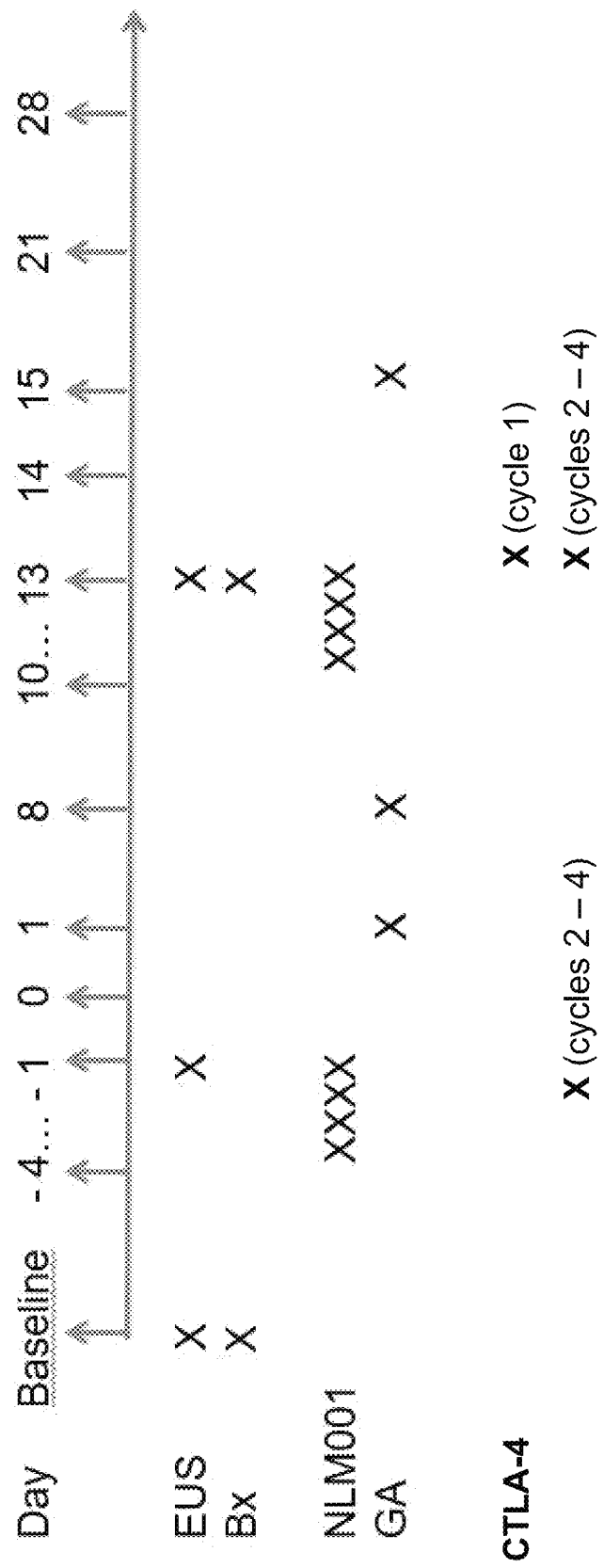
FIG. 8 is an example of a treatment regimen including: NLM-001: 800 mg/day oral days −4 to −1 and 10-13 of each cycle of cycles 1-3: Gemcitabine (G): 1.000 mg/m$^2$ IV days 1, 8, and 15 every 28 days: Abraxane (A): 125 mg/m$^2$IV days 1, 8, and 15 everv 28 days; and a CTLA-4 inhibitor (CTLA-4): 1 mg/kg on day 15 of cycle 1 and days 1 and 15 in subsequent cycles.

As another example, a treatment regimen may include: NLM-001: 800 mg/day oral days −4 to −1 and 10-13 of each cycle of cycles 1-3; Gemcitabine (G): 1,000 mg/m² IV days 1, 8, and 15 every 28 days; Abraxane (A): 125 mg/m²IV days 1, 8, and 15 every 28 days; and a CTLA-4 inhibitor (CTLA-4): 1 mg/kg on day 15 of cycle 1 and days 1 and 15 in subsequent cycles, FIG. 8 is illustrative.

As above in Example 2, tumor elasticity is measured by endoscopic ultrasound with elastography on baseline and on days −1 and 13 of Cycle 1. A biopsy of the primary tumor is carried out simultaneously at baseline and Cycle 1 Day 13. After the first cycle, patients continue treatment until disease progression or unacceptable toxicity. Also, improvement endpoints remain as described in Example 2.

Prophetic Examples 2 and 3, together, provide direction to demonstrate that a transient, so-called "shock" administration of TAK 441, in patients with advanced pancreatic cancer transiently reduces the stroma of pancreatic cancer, thereby favoring the effects of chemotherapy treatment.

Example 4 (Prophetic)

Hepatocellular carcinoma (HCC) is a deadly tumor for which the incidence is increasing in the United States, primarily due to prevalence of hepatitis C infection. HCC is the most frequent primary liver cancer and the second leading cause of cancer death worldwide. See, Ferlay J, Soerjomataram I, Dikshit R, Eser S, Mathers C, Rebelo M, et al. Cancer incidence and mortality worldwide: sources, methods and major patterns in GLOBOCAN 2012. Int J Cancer. 2015; 136(5):E359-E386. doi: 10.1002/ijc.29210. Despite significant progress in the diagnosis and treatment of HCC, its prognosis remains extremely poor with a 5-year overall survival (OS) rate of 12%, all stages taken together Id. Most HCCs (80-90%) develop on underlying chronic liver disease (with or without cirrhosis); the main causes include chronic hepatitis B virus (HBV) or hepatitis C virus (HCV) infections, alcohol consumption, non-alcoholic steatohepatitis, or other less frequent etiologies such as hemochromatosis, tobacco and aflatoxin B1. The highest incidence of HCC is observed in South-East Asia and Central Africa, where the endemic prevalence of chronic HBV infections accounts for 70% of cases. See, e.g., Pawlotsky J M. Pathophysiology of hepatitis C virus infection and related liver disease. Trends Microbiol. 2004; 12(2):96-102; Trepo C, et al., Hepatitis B virus infection. Lancet. 2014; 384(9959):2053-2063; Morgan T R, et al., Alcohol and hepatocellular carcinoma. Gastroenterology, 2004; 127 (5 Suppl 1):S87-S96; Zhang D Y, et a., Fibrosis-dependent mechanisms of hepatocarcinogenesis. Hepatology. 2012; 56(2):769-775; Bugianesi E, et al., NASH and the risk of cirrhosis and hepatocellular carcinoma in type 2 diabetes. Curr Diab Rep. 2007; 7(3):175-180; Fomer A, et al., Hepatocellular carcinoma. Lancet. 2012; 379(9822):1245-1255; and Llovet J M, Zucman-Rossi J, Pikarsky E, Sangro B, Schwartz M, Sherman M, et al. Hepatocellular carcinoma. Nat Rev Dis Prime. 2016, each incorporated by reference with regard to the background on HCC.

The "Barcelona Clinic Liver Cancer" (BCLC) classification is currently recommended to assess the prognosis and choose the most appropriate treatment for HCC patients (available online at https://www.esmo.org/Guidelines/Gastrointestinal-Cancers/Hepatocellular-Carcinoma). There are five BCLC classes (0, A, B, C and D) which take into consideration both the underlying liver function, as assessed by the Child-Pugh score, and the patient's general condition according to the Eastern Collaborative Oncology Group Performance Status (ECOG PS). The only curative treatments for HCC, reserved to patients with early-stage HCC (BCLC stage 0, A), are surgical resection, thermal ablation, radiotherapy and/or liver transplantation. No adjuvant treatment has been validated for HCC Hedgehog signaling promotes tumor-associated macrophage polarization to suppress intratumoral CD8+ T cell recruitment. See, Petty et al, *Journal of Clinical Investigation* (2019), herein incorporated by reference with regard to such testing protocol. The compound of the present disclosure, TAK-441, may be given in combination with a PD-1 blockade to provide synergistic efficacy. Reference may also be made to the article: Scientists discover reasons why targeted immuno-oncology drugs sometimes fail (2019, October 23), from https://medicalxpress.com/news/2019-10-scientistsimmuno-oncology-drugs.html, herein incorporated by reference with regard to such testing protocol. This synergy may be particularly suited to the treatment of HCC.

PD-1 is a checkpoint protein on T cells, a type of immune cell that helps the body recognize abnormal cells and disease in the body. PD-1 normally acts as an "off switch" that helps keep T-cells from attacking other cells. PD-1 inhibitors are used to selectively block this protein and boost immune response to attack cancer cells. Previously reported data has shown that a primary reason some cancer patients do not respond to the PD-1 therapy is the inability of the fighter T cells (known as CD8 T cells) to invade the tumor microenvironment, a state also known as "cold tumors." In their study, Yang et al., report data showing the specific cellular mechanisms that limit the ability of CD8 T cells to infiltrate the tumor microenvironment. They show that Hedgehog signaling shut down chemokine secretion by tumor-associated macrophages-which is critical to CD8 T-cell infiltration. By blocking (inhibiting) the hedgehog pathway, the researchers were able to reverse the process and promote CD8 T-cell infiltration into the tumor microenvironment. The data demonstrated that hedgehog inhibitors given in combination with a PD-1 blockade were more effective in killing cancer cells than a single agent alone in preclinical models, including both liver and lung cancer.

The hedgehog (HH) pathway is involved in the embryonic development of liver, and its reactivation plays a substantial role in sustaining cancer cell growth and progression in hepatocellular carcinoma (HCC). In hepatocarcinogenesis, HH signalling is required for differentiation, proliferation and polarity of liver embryonic cells. High levels of expression of HH components in HCC tissues correlate with mesenchymal properties and maintain the proliferation of cancer stem cells, which is a dynamic source of malignant cells in HCC progression. Current data on HH inhibition in preclinical models further confirm the role of HH and deserve future investigations in a clinical setting. See., e.g., Implication of the Hedgehog pathway in hepatocellular carcinoma, Della Corte, et al., World J Gastroenterol. 2017 Jun. 28; 23(24): 4330-4340. Published online 2017 Jun. 28.

Examples of checkpoint inhibitors may include one or more PD-1 inhibitors such as pembrolizumab (KEYTRUDA®), nivolumab (OPDIVO®), and cemiplimab (LIBTAYO®); PD-L1 inhibitors such as atezolizumab (TECENTRIQ®), avelumab (BAVENCIO®), and durvalumab (IMFINZI®); and CTLA-4 inhibitors such as ipilimumab (YERVOY®). Additional checkpoint inhibitors include tremelimumab, AGEN1884, AGEN2034, or AGEN1181.

Study Description

A phase I/II clinical trial that is one or more of open, multicenter, and non-randomized as in Example 2, additionally adding administration of a checkpoint inhibitor, such as a PD1 or CTLA4 inhibitor as herein noted.

Hedgehog inhibitor TAK-441, which may also be referred to as NLM001, may be administered for 4 cycles, at a dose of 800 mg/day (one dose below the maximum previously administered) for 5 days. At the end of each cycle, the administration is followed by administration of a checkpoint inhibitor. The combination is believed to demonstrate an effect above what is demonstrated by either single agent individually.

In one aspect of the examples provided herein, the improvement to a patient is evidenced by one or more of:
  metabolic responses,
  positron emission tomography,
  objective responses according to criteria,
  progression-free survival,
  overall survival,
  responses based on levels of a tumor marker,
  toxicity, and
  elasticity of the tumor.

In this regard, metabolic responses, may be measured by fluorodeoxyglucose (FDG), PET may be evaluated according to EORTC criteria, objective responses may be evaluated according to RECIST (Response Evaluation Criteria in Solid Tumors) criteria, progression free survival is as defined herein, overall survival, is as defined herein, responses based on levels of a tumor marker may be evaluated against, for example, CA 19.9, toxicity may be evaluated according to, for example, Common Toxicity Criteria for Adverse Events Terminology, National Cancer Institute, version 4.03 (NCI CTCAE v4.03)), and elasticity of the tumor may be evaluated by elastography defined as the quotient strain ratio between the tumor tissue and normal tissue.

All subjects will be included in the efficacy analysis according to the principle "by treatment intention". All subjects who have received at least the first dose of the first cycle of treatment will be included in the toxicity analysis.

The elasticity index will be represented graphically for each subject and measurement time. For each patient, the variation in this parameter will be calculated for each measurement point. The values of the different points will be compared by means of non-parametric tests for paired samples. The variations in CA 19.9 will be analyzed in the same way.

The objective responses by CT and/or MRI will be analyzed according to the RECIST criteria, attributing a response to each subject. The global data of the study will be summarized using descriptive statistics. The responses by PET will also be analyzed using the EORTC criteria.

Biomarker analysis will be presented graphically for each subject. The data will be summarized using descriptive statistics for each collection point, including the calculation of proportional variation before and after treatment and comparison by nonparametric methods for paired samples. Globally we will use the methodology previously published in the studies with GA.

Likewise, the pharmacokinetic parameters will be represented and visualized graphically and summarized using descriptive statistics.

Adverse Events as characterized by type, frequency, severity (as graded by National Cancer Institute Common Terminology Criteria for Adverse Events (NCI CTCAE) version 4.03), timing, seriousness, and relationship to study therapy will be described using descriptive statistics.

Overall survival is defined as the time elapsed between the date of inclusion and the date of death. Progression-free survival is defined as the time elapsed between the date of inclusion and the date of progression, the start of a second-line treatment with no documented progression or death. Both variables will be studied with survival curves according to the Kaplan-Meier method.

Considering the exploratory nature of the study design, it is not considered necessary to apply corrections for the multiplicity of the tests used.

The level of significance used in all statistical tests will be the value of p=0.05 bilateral.

The details of the analysis will be reflected in the statistical analysis plan that will be prepared before the closure of the study database.

All publications, patents and patent applications cited in this specification are incorporated herein by reference for the teaching to which such citation is used.

Test compounds for the experiments described herein were employed in free or salt form.

The specific responses observed may vary according to and depending on the particular active compound selected or whether there are present carriers, as well as the type of formulation and mode of administration employed, and such expected variations or differences in the results are contemplated in accordance with practice of the present invention.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

What is claimed is:

1. A method for treating a subject having a cancerous tumor, the method comprising
  transient administration of TAK-441 as a hedgehog inhibitor (HHI) to the subject in combination with one or more additional cancer therapies,
  wherein the one or more additional cancer therapies are administered in one or more cycles of treatment, wherein the one or more cycles of treatment include a treatment regimen comprising:
  (a) administration of TAK-441 prior to administration of the one or more additional cancer therapies;
  (b) administration of the one or more additional cancer therapies; and
  (c) a repeat of step (a) and step (b) until the one or more cycles of treatment are complete; and
  wherein the administration of TAK-441 does not continue throughout all cycles of treatment.

2. The method of claim 1, wherein the administration of TAK-441 is discontinued prior to initiating clinically significant detrimental fibroblast depletion.

3. The method of claim 1, wherein TAK-441 is administered prior to the administration of at least one additional cancer therapies.

4. The method of claim 1, wherein the administration of TAK-441 is discontinued prior to discontinuation of at least one of the additional cancer therapies.

5. The method of claim 1, wherein at least one of the additional cancer therapies is a systemically delivered therapy.

6. The method of claim 5, wherein the systemically delivered therapy is chemotherapy, targeted therapy, or immunotherapy.

7. The method of claim 1, wherein the tumor is at least one of a fibrotic tumor, a solid tumor, and a tumor having high stromal content.

8. The method of claim 1, wherein TAK-441 reduces stromal content; induces angiogenesis in or around the tumor; and/or improves tumor uptake of a subsequently administered chemotherapeutic agent.

9. The method of claim 1, wherein the administration of TAK-441 improves the efficacy of the subsequently administered cancer therapy.

10. The method of claim 1, wherein the cancer is pancreatic cancer, esophageal cancer, squamous cell carcinoma, prostate cancer, colon cancer, breast cancer, hepatocellular carcinoma, renal cancer, or cholangiocarncinoma.

11. The method of claim 1, wherein the cancer is pancreatic ductile adenocarcinoma (PDAC).

12. The method of claim 5, wherein the systemically delivered therapy is a chemotherapeutic agent selected from the group consisting of gemcitabine, nab-paclitaxel, taxol, irinotecan, temozolomide, capecitabine, topotecan, cisplatin, oxaliplatin, carboplatin, camptothecin, cytarabine, fluorouracil, cyclophosphamide, etoposide phosphate, teniposide, doxorubicin, daunorubicin, and pemetrexed.

13. The method of claim 1, wherein the route of administration for the TAK-441 is selected from the group consisting of intravenous, oral, and topical.

14. The method of claim 1, wherein the route of administration for the additional cancer therapy is selected from the group consisting of intravenous, oral, and topical.

15. The method of claim 1, wherein the subject receives cycles of treatment of the additional cancer therapy and TAK-441 is administered during fewer than all of cycles of treatment.

16. The method of claim 1, wherein each cycle of treatment is 28 days and the TAK-441 is administered on days −4 to −1 and 10-13 on at least one cycle of treatment and the chemotherapeutic agent is administered on days 1, 8, and 15 per each cycle of treatment.

17. The method of claim 16, wherein the TAK-441 is an 800 mg dose.

18. The method of claim 16, wherein the chemotherapeutic agent is selected from one or more of 1000 mg/m$^2$ of Gemcitabine and 125 mg/m$^2$ nab-paclitaxel.

19. The method of claim 16, further comprising administration of a Checkpoint Inhibitor (CI) during at least one cycle of treatment.

20. The method of claim 19, wherein the CI is a CTLA 4 inhibitor, a PD1 inhibitor, or a PDL1 inhibitor.

21. The method of claim 20, wherein the CI is Tremelimumab, Ipilimumab, Durvalumab, Nivolumab, Pembrolizumab, Atezolizumab, Cemiplimab, AGEN1884, AGEN2034, or AGEN1181.

22. The method of claim 21, wherein the CI is Ipilimumab.

23. The method of claim 19, wherein the subject receives treatment in cycles and the one or more doses of CI is only administered near the end of or the beginning of a treatment cycle.

24. The method of claim 19, wherein the CI dose is a 3 mg/kg IV dose of Ipilimumab.

25. The method of claim 1, further comprising a rest day after administration of TAK-441 and/or administration of the one or more additional cancer therapies.

26. The method of claim 19, wherein each cycle of treatment is 28 days and the CI is administered on day 15, or day 1 and day 15, for each cycle of treatment.

* * * * *